(12) United States Patent
Edmunds et al.

(10) Patent No.: US 10,000,259 B2
(45) Date of Patent: Jun. 19, 2018

(54) SUCTION ANCHOR

(71) Applicant: UTEC GEOMARINE LIMITED, Norwich (GB)

(72) Inventors: James Edmunds, Northumberland (GB); Jonathan Bruce Machin, Northumberland (GB); Peter Gerard Allan, Northumberland (GB)

(73) Assignee: UTEC Geomarine Limited, Norwich (GB)

( * ) Notice: Subject to any disclaimer, the term of this patent is extended or adjusted under 35 U.S.C. 154(b) by 97 days.

(21) Appl. No.: 15/025,007

(22) PCT Filed: Sep. 25, 2014

(86) PCT No.: PCT/GB2014/052909
§ 371 (c)(1),
(2) Date: Mar. 25, 2016

(87) PCT Pub. No.: WO2015/044667
PCT Pub. Date: Apr. 2, 2015

(65) Prior Publication Data
US 2016/0236755 A1 Aug. 18, 2016

(30) Foreign Application Priority Data
Sep. 26, 2013 (GB) .................................. 1317140.0
Feb. 8, 2014 (GB) .................................. 1402199.2

(51) Int. Cl.
*B63B 21/27* (2006.01)
*E02D 19/12* (2006.01)
(Continued)

(52) U.S. Cl.
CPC .............. *B63B 21/27* (2013.01); *E02D 19/12* (2013.01); *G01N 1/08* (2013.01); *G01N 3/42* (2013.01);
(Continued)

(58) Field of Classification Search
CPC ......... B63B 21/24; B63B 21/26; B63B 21/27; B63B 21/30; B63B 21/50;
(Continued)

(56) References Cited

U.S. PATENT DOCUMENTS 6,463,801 B1 * 10/2002 Young ...................... E02D 1/04
73/170.32
6,488,446 B1 * 12/2002 Riemers .................. B63B 21/27
114/296

FOREIGN PATENT DOCUMENTS

| GB | 2 478 858 | 9/2011 |
| WO | WO 97/30889 | 8/1997 |
| WO | WO 2012/129612 | 10/2012 |

OTHER PUBLICATIONS

International Search Report for PCT/GB2014/052909 dated Dec. 3, 2014, 3 pages.

* cited by examiner

*Primary Examiner* — Benjamin Schmitt
(74) *Attorney, Agent, or Firm* — Nixon & Vanderhye P.C.

(57) ABSTRACT

A suction anchor for a remotely operated vehicle comprising a frame attachable to a remotely operated vehicle, anchor cans beneath the frame beneath and connectable to a pump. In particular the anchor can be deployed as part of a method for sampling or measuring the seabed comprising the steps of attaching a frame to the remotely operated vehicle, the frame having one or more downwardly mounted anchor cans and a mast to which sampling and/or measuring equipment is attached, placing the anchor cans on an underwater floor, and, at least in partially, evacuating the cans of water embedding them in part into the underwater floor, sampling and/or measuring the underwater floor using the sampling and/or measuring equipment. It can be used to mount other sensor equipment requiring a stable platform.

13 Claims, 2 Drawing Sheets

(51) Int. Cl.
  *G01N 1/08* (2006.01)
  *G01N 3/42* (2006.01)
  *G01N 33/24* (2006.01)
  *B63B 21/26* (2006.01)

(52) U.S. Cl.
  CPC ........ *G01N 33/24* (2013.01); *B63B 2021/267* (2013.01)

(58) Field of Classification Search
  CPC ...... B63B 2021/006; G01N 1/02; G01N 1/08; G01N 33/24; G01D 11/30; E21B 25/18; E02D 1/025
  USPC ....................... 73/170.32; 114/294, 296, 311
  See application file for complete search history.

SUCTION ANCHOR

This application is the U.S. national phase of International Application No. PCT/GB2014/052909 filed 25 Sep. 2014 which designated the U.S. and claims priority to GB Patent Application No. 1317140.0 filed 26 Sep. 2013 and GB Patent Application No. 1402199.2 filed 8 Feb. 2014, the entire contents of each of which are hereby incorporated by reference.

TECHNICAL FIELD

This invention relates to a suction anchor for increasing the stability and reaction force available to investigate the soil properties of the seabed or other underwater floors by penetrating with a probe, soil sampling tool, or other seafloor sensor equipment.

BACKGROUND

In-situ underwater floor testing and sampling requires an amount of reaction force to allow tooling (measuring probe or sampling tooling) to penetrate the underwater floor at any given test location. Conventional delivery systems achieve this means of heavy lift crane deployed frames and applying ballast to the frame on which the testing equipment is mounted. Other larger systems exist which test directly from a jack up barge. Both systems can be relatively accurately deployed but the only practical method of ensuring precision accuracy in test location deployment is the use of a subsea Remotely Operated Vehicle (ROV). In the case of the ROV mounted system; applying ballast is not a practical solution as this affects the manoeuvrability of the ROV. As the ROV is essentially neutrally buoyant, the use of thrusters is the only means currently available by which additional reaction force can be achieved; this limits both the soil conditions that can be tested and depth of penetration that can be achieved. An ROV mounted tool is capable of testing under structures and can safely test alongside existing seabed structures without risking damage where a wire lift system is limited.

In-situ underwater floor testing and sampling requires an amount of reaction force to allow tooling (measuring probe or sampling tooling) to penetrate the underwater floor at any given test location. Conventional delivery systems achieve this means of heavy lift crane deployed frames and applying ballast to the frame on which the testing equipment is mounted. Other larger systems exist which test directly from a jack up barge. Both systems can be relatively accurately deployed but the only practical method of ensuring precision accuracy in test location deployment is the use of a subsea Remotely Operated Vehicle (ROV). In the case of the ROV mounted system; applying ballast is not a practical solution as this affects the manoeuvrability of the ROV. As the ROV is essentially neutrally buoyant, the use of thrusters is the only means currently available by which additional reaction force can be achieved; this limits both the soil conditions that can be tested and depth of penetration that can be achieved. An ROV mounted tool is capable of testing under structures and can safely test alongside existing seabed structures without risking damage where a wire lift system is limited.

DISCLOSURE OF INVENTION

According to the present invention a suction anchor for use underwater comprising a frame of T-shape in plan, comprising a stem, a cross piece, mounting points on the stem to receive an underwater submersible vehicle, and at least two anchor cans capable of evacuation mounted beneath the cross piece one towards the each end of the cross piece.

In another aspect of the invention a method of anchoring to the sea bed a mounting frame for test equipment, comprises the steps of attaching a submersible to the stem of a T-shaped frame of a suction anchor, the T-shaped frame comprising a stem and cross piece, the frame having at two anchor cans capable of evacuation towards the ends of the cross piece, placing the anchor cans on the sea bed, anchoring the T-frame by at least partially evacuating the anchor cans of water.

DESCRIPTIONS OF EXAMPLES OF THE INVENTION

Figure 1:
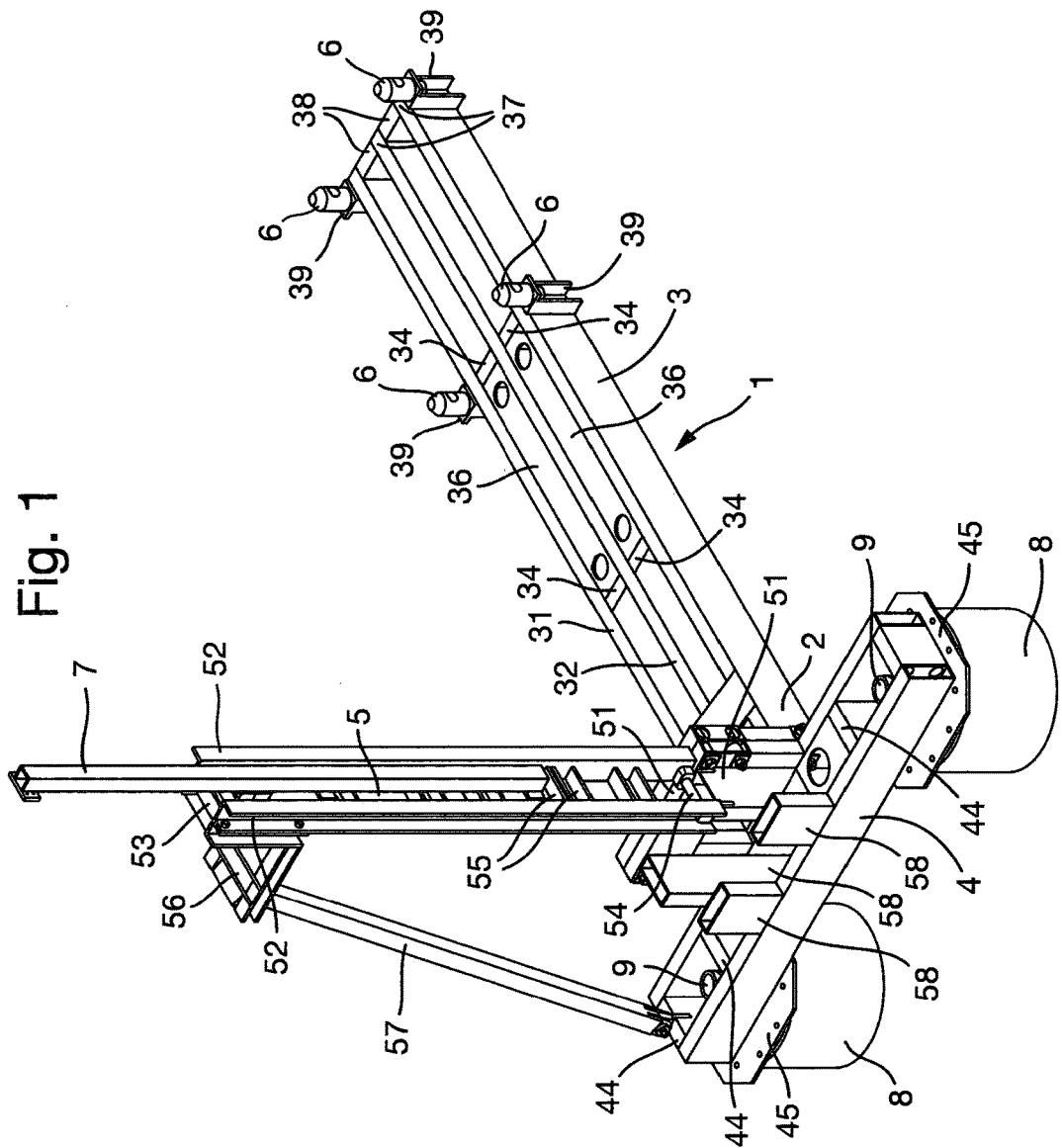
FIG. 1 is an isometric view of one configuration of the anchor of the present invention before connection to an ROV host.

FIG. 1 shows an example of anchor 1 according to the present invention. The anchor comprises a T-shaped horizontal frame or skid 2, with the stem 3 and cross piece 4. Rising vertically from the interaction of the stem 3 and cross piece 4 is a tooling mast 5 to which test equipment to sample the sea-bed (not shown in FIG. 1) may be attached. On the stem 3 are mounting points 6 for attachment to a host ROV. Rising from and attached to the tooling mast 5 is a cable management mast 7. Towards each end of the cross piece 4 and directed downwards from the T-shaped skid 2 are two suction anchor cans 8, one towards each end to the cross piece 4.

Figure 2:
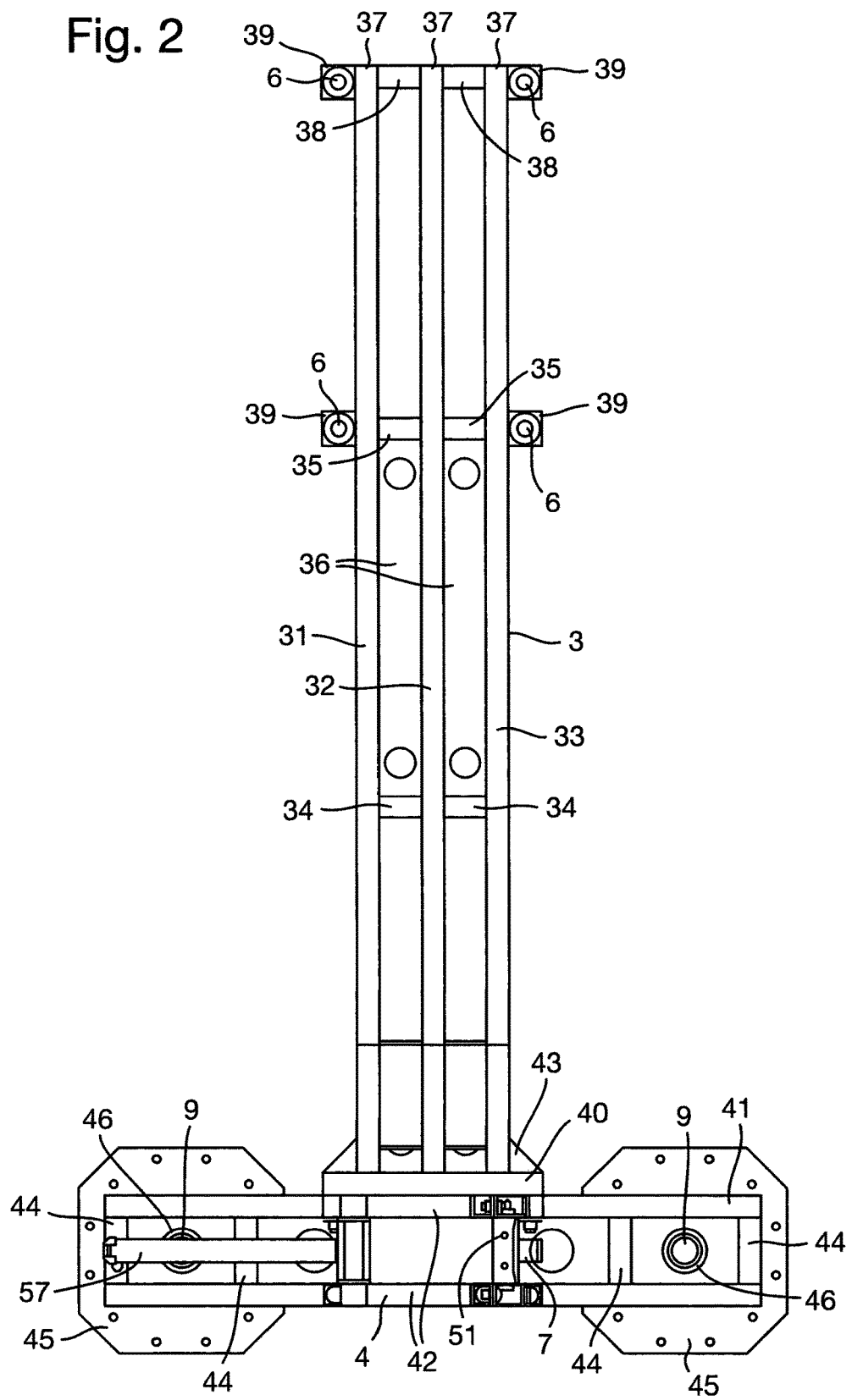
FIG. 2 is a plan elevation showing the hose tail ports (5) into the suction anchor cans which allow fluid to be extracted creating the negative pressures within the suction anchor cans.

In FIG. 2 ports 9 can be seen to which a conventional zip or dredge pump is connected to the suction anchors cans 8.

The suction anchor 1 is assembled out of water and attached to a host submersible such as a remotely operated vehicle (ROV) with industry standard pins through the mounting points 6 or by use or other mounting method. The desired testing or sampling equipment is attached to the tooling mast 5; examples of testing or sampling equipment include but are not limited to cone penetrometers, T-bar penetrometers, pressure meters, pistons samplers, liner samplers or Shelby tube samplers. Any necessary cabling is run through the cable management mast 7. A device for pumping water from the anchor cans, such as an anchor zip or dredge pump is attached via hoses ports 9 on the suction anchor cans 8. The ROV then maneuvers the anchor to a desired location on the sea-bed. When located in the desired location, the suction anchor cans 8 will penetrate the sea bed a small amount allowing a seal to form such that when water is partially evacuated the anchor cans 8, the cans will penetrate further into the underwater floor until such time as the cans are either fully embedded or the pumping is discontinued. Discontinuation of pumping could be achieved either by switching off the pumping device or by the closure of one or more inline valves thereby isolating individual or multiple cans and preventing free-flooding.

Monitoring of flow pressures and penetration rates during installation can be performed and recorded for later interpretation.

Once embedded, an amount of skin friction between the surroundings and sea bed material trapped in the suction cans 8 will be exerted onto the suction anchor cans' 8 internal and external surfaces. It is this skin friction and the optionally closed can that will provide the reaction force required for penetration testing or sampling of the underwater floor by the particular tool mounted.

Extraction of the system is achieved by pumping water or air back into the suction anchor cans to generate a positive pressure inside and thereby lifting the cans and skip free. The ROV can the raise the anchor to the surface. In the event that this is insufficient force to extract the system, an emergency breakaway system will be employed to facilitate extraction. This can take several forms, including but not limited to, additional lifting points, weak links, hydraulic rams or the ability to completely disconnect from the host ROV and leave the anchor, mounted test equipment and cables on the seabed for subsequent extraction by crane.

The stem 3, cross piece 4 and tooling mast 5, may each comprise frames. For example as seen in the drawings the stem 3 comprises three parallel elongate members 31, 32 and 33. They are spaced apart by short intermediate members 34 and 35 welded at each of their ends to each of a pair of the longitudinal members (31 and 32 or 32 and 33) approximately one third and two thirds respectively along the length of the longitudinal members. Two plates 36 are welded one into each of the rectangles formed between the intermediate cross members 34 and 35 and the longitudinal members 31, 32, and 33. The plates 36 are at the tops of the rectangles. The gaps between distal ends 37 of the longitudinal members 31, 32, 33 (i.e. the ends of the longitudinal members 31, 32, and 33 away from the cross piece 4) are closed with further cross members 38. Inverted flat bottom U-shaped members 39 are welded to the outer most surfaces of longitudinal members 31, and 33, the flat inverted surfaces of the U-shaped members 39 have the mounting points 6 supported on them.

The proximal ends of the longitudinal members 31, 32, 33 have a transverse end member 40 welded to then which is bolted to a member 41 being part of the cross piece 4. The join between end member 40 and member 41, is supports from beneath by a plate 43, bolted or welded to longitudinal members 31, 32 and 33, the end member 40 to member 41.

Cross piece 4 comprises a frame made up of pair of parallel members 41 and 42 separated by short bracing members 44 welded or bolted to the members 41 and 42, the short bracing members 43 being transverse to the cross piece 4. Mounted beneath the parallel members 41 and 42 and the short bracing members 43 are two plates 44 one towards one end of the cross piece 4 the other towards the other end. The anchor cans 8 are bolted beneath these plates. The plates have holes 46 through which the ports 9 pass.

Extending upwards from the cross piece 4, is a mounting plate 51 for the tooling mast 5. The tooling mast comprises pair of parallel up right members 52, separated by cross pieces 53 and 54 top and bottom. A series of steps 55 enable people to climb the tooling mast. Atop the tooling mast is a large angle bracket piece 56 onto which sea bed sampling equipment and/or sea bed penetration equipment can be mounted is mount. This equipment can drill down into the sea bed though the gap 47 formed mid-way along the cross piece 4. The bracket 56 is supported also by a bracing member 57, bolted to one of the outermost of the short bracing members 44. Other mounting points 59 are provided to mount equipment to control, operate or monitor the sampling and/or sea bed penetration devices supported on bracket 56. Power supplies to the equipment are provided through the cable management mast 7, which is bolted to cross piece 53.

In addition to testing and sampling equipment that can mounted on the tooling mast 5, and which needs a stable reactive mounting to penetrate the sea, other equipment such as cameras and laser measuring devices can be hosted on the anchor 1, on the stem 3, cross piece or the tooling mast 5 to provide non-penetrative analysis of the seabed in the vicinity of the anchor.

The invention claimed is:

1. A suction anchor for use underwater comprising a frame of T-shape in horizontal plan, comprising a stem, a cross piece, a plurality of mounting points on the stem to mount and attach an underwater submersible vehicle, and at least two anchor cans capable of evacuation attached to and mounted beneath the cross piece, one anchor can towards each end of the cross piece.

2. The suction anchor according to claim 1 additionally comprising a tooling mast extending perpendicular upwards from the intersection of the stem and cross piece.

3. The suction anchor according to claim 2 additionally comprising a cabling mast through which control cables may be passed.

4. The suction anchor according to claim 1 in which the underwater submersible vehicle is a remotely operated vehicle.

5. A method of anchoring to the sea bed a mounting frame for test equipment, comprising the steps of attaching a submersible to a plurality of mounting points on the stem of a T-shaped frame of a suction anchor, the T-shaped frame in horizontal plan comprising a stem and cross piece, the frame having at least two anchor cans attached to and mounted below the cross piece, one anchor can towards each end of the cross piece and capable of evacuation, placing the anchor cans on the sea bed, anchoring the T-shaped frame by at least partially evacuating the anchor cans of water.

6. The method according to claim 5 additionally comprising releasing the T-shaped frame and submersible from the sea bed by pumping air or water into the anchor cans.

7. The method according to claim 5 comprising releasing the T-shaped frame and submersible by disconnecting the anchor cans from the cross member.

8. The method according to claim 5 additionally comprising mounting sea-bed penetrating equipment on a tooling mast, said mast extending vertically upwards vertically form the inter-section of the stem and cross piece.

9. The method according to claim 8 including the step of sampling the sea-bed using the sampling and/or measuring equipment mounted on the tooling mast.

10. The method according to claim 8 including the step of monitoring the sea-bed using monitoring equipment mounted on the tooling mast.

11. The method according to claim 5 additionally comprising passing cables though a cable mast.

12. The method according to claim 5 including the step of monitoring the sea-bed using monitoring equipment mounted on the T-frame.

13. The method of anchoring to the seabed the mounting frame according to claim 5 said method comprising a step of stabilising sensors for measuring the surrounding environment or structures.

* * * * *